United States Patent
Hoorn et al.

(10) Patent No.: US 6,835,853 B2
(45) Date of Patent: Dec. 28, 2004

(54) PROCESS FOR RESOLUTION OF TAMSULOSIN AND COMPOUNDS, COMPOSITIONS, AND PROCESSES ASSOCIATED THEREWITH

(75) Inventors: Hans J Hoorn, Nijmegen (NL); Theodorus H. A. Peters, Arnhem (NL); Jaroslav Pis, Praha (CZ); Radim Scigel, Praha (CZ)

(73) Assignee: Synthon BV, Nijmegen (NL)

( * ) Notice: Subject to any disclaimer, the term of this patent is extended or adjusted under 35 U.S.C. 154(b) by 0 days.

(21) Appl. No.: 10/208,009

(22) Filed: Jul. 31, 2002

(65) Prior Publication Data

US 2003/0109752 A1 Jun. 12, 2003

Related U.S. Application Data

(60) Provisional application No. 60/330,817, filed on Oct. 31, 2001.

(51) Int. Cl.[7] ............................................. C07C 303/44
(52) U.S. Cl. ......................................................... 564/86
(58) Field of Search ............................................ 564/86

(56) References Cited

U.S. PATENT DOCUMENTS

| 4,217,305 | A | 8/1980 | Imai et al. |
| 4,731,478 | A | 3/1988 | Niigata et al. |
| 6,335,467 | B1 * | 1/2002 | Englert et al. ................. 564/86 |
| 6,528,685 | B2 * | 3/2003 | Cohen et al. ................ 564/215 |

FOREIGN PATENT DOCUMENTS

| EP | 0 034 432 B1 | 8/1981 |
| EP | 0 257 787 B1 | 3/1988 |

* cited by examiner

*Primary Examiner*—Peter O'Sullivan
(74) *Attorney, Agent, or Firm*—Mark R. Buscher

(57) ABSTRACT

Optically impure tamsulosin including racemic tamsulosin can be resolved into optically pure (R)- or (S)-tamsulosin by the use of diastereomeric sulfonate salts of tamsulosin in a fractional crystallization technique. Racemic tamsulosin free base is a useful starting material for the resolution process and a method of obtaining the same in solid form, including two crystalline polymorphic forms, is also provided.

38 Claims, 6 Drawing Sheets

PROCESS FOR RESOLUTION OF TAMSULOSIN AND COMPOUNDS, COMPOSITIONS, AND PROCESSES ASSOCIATED THEREWITH

This application claims the benefit of priority under 35 U.S.C. § 119(e) from provisional patent application Ser. No. 60/330,817, filed Oct. 31, 2001, the entire contents of which are incorporated herein by reference.

BACKGROUND OF THE INVENTION

The present invention relates to a process for the resolution of (R,S)-5-[2-[[2-(2-ethoxyphenoxy)ethyl]amino]propyl]-2-methoxybenzene-sulfonamide, also known as tamsulosin, into optically enriched and/or optically pure enantiomers and to compounds and compositions useful therein as starting materials, including solid racemic tamsulosin free base and a process of producing the same, and to products thereof.

The compound 5-[2-[[2-(2-ethoxyphenoxy)ethyl]amino]propyl]-2-methoxy-benzenesulfonamide of the formula (1)

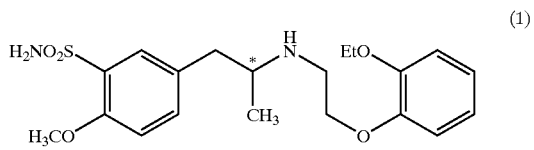

is a commercially marketed pharmaceutically active substance useful for the treatment of cardiac insufficiencies and benign prostatic hyperplasia. It is disclosed in EP34432 and U.S. Pat. No. 4,731,478. The molecule, which will be further denoted as "tamsulosin," has one asymmetric carbon (indicated by an asterisk in the above formula (1)), thus allowing for the existence of two enantiomers, conventionally denoted as (R)- or (S)-enantiomers. Both the free base and its acid addition salts may comprise either one or both of the two enantiomers. The single enantiomers have distinctive optical activity in polarized light and they also differ in their pharmaceutical activities. The commercially marketed product is the hydrochloride salt of the (R)-enantiomer of tamsulosin which is levorotary or (R)(-) tamsulosin hydrochloride.

EP34432/U.S. Pat. No. 4,731,478 discloses, inter alia, two general processes that may provide tamsulosin. One general process (hereinafter "process A") comprises a reductive amination of a benzylmethylketone compound with a substituted phenoxyethylamine. To make tamsulosin, the corresponding species would be represented by formulae (4) and (5), respectively.

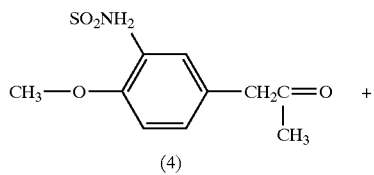

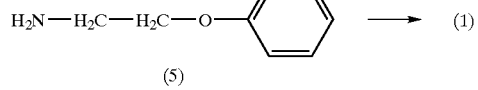
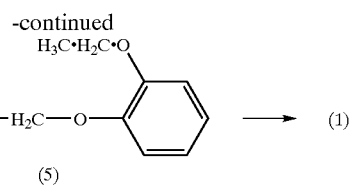

However, neither these compounds nor the details of an actual production process leading to tamsulosin using this process is set forth. Instead, process A was exemplified only for alkylsulfonamide derivatives. Accordingly, the compounds (4) and (5) were also not prepared as chemical entities. Further, the exemplified products of process A, see examples 4 and 5, were crystallized as the hydrochloride salt of the racemate. If process A is applied for the synthesis of tamsulosin, the result would allow for producing a racemic tamsulosin isolated in the form of a hydrochloride salt and not as the free base.

The second process (hereinafter "process B") generically teaches conversion of a hydroxylated analogue into the desired sulfonamide via a chloro-analogue. For making tamsulosin, the hydroxy analogue would be a compound of formula (8).

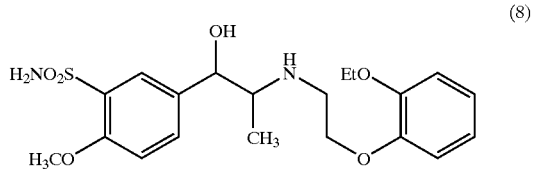

It was disclosed therein that the starting hydroxy-analogues may be prepared according to the methods of GB 2006772, which correspond to DE 2843016 and U.S. Pat. No. 4,217,305. However, none of these documents specifically show the formation of this hydroxy-tamsulosin intermediate compound. Further, it appears in both U.S. Pat. No. 4,731,478 and GB 2006772 that only racemic tamsulosin and racemic hydroxy-tamsulosin, respectively, would be prepared by this general reaction scheme, and not the pure enantiomer. Note that tamsulosin was not prepared by this process in U.S. Pat. No. 4,731,478. It can be derived that condensation of the compound (5) with a suitable reaction partner (geminal halohydrin or oxiran), according to GB 2006772, would produce racemic hydroxy-tamsulosin that would then be correspondingly converted to racemic tamsulosin. Moreover, as in process A, the examples for the related compounds, Examples 1–3, are isolated as HCl salts via crystallization and not as the free base.

While U.S. Pat. No. 4,731,478 does disclose racemic tamsulosin HCl in Example 20, it does not show how the compound was made. Apparently the compound was isolated as the HCl salt and not as the free base.

A method of resolution of racemic tamsulosin into optical isomers was not disclosed in above prior art documents. The only process disclosed in U.S. Pat. No. 4,731,478 that obtains optically pure enantiomeric forms is not in accord with process A or process B, but instead comprises reacting optically pure 5-((2-amino-2-methyl)ethyl)-2-methoxybenzenesulfonamide with 2-(o-ethoxyphenoxy)ethyl bromide to form the corresponding (R)- or (S)-tamsulosin. See Examples 33(a) and 33(b). Known processes for providing the optically pure amine, e.g. processes disclosed in JP 58-18353, EP257787, JP 02-679248, are lengthy and complicated. If the starting amine does not have a desired optical purity, the produced tamsulosin would accordingly be prepared in an optically impure form (in a mixture of enantiomers). No method is known how to purify such an optically impure product.

It would be desirable to have a method to resolve optically impure tamsulosin, including racemic tamsulosin. Specifically, it is desirable to provide a process for the resolution of a racemic tamsulosin or a mixture of tamsulosin enantiomers, which could manufacture the desired enantiomer, particularly the (R) enantiomer, in a desired purity. But to carry out such a resolution method, it would be further desirable to first provide tamsulosin free base, especially racemic tamsulosin free base, in solid state and preferably in a relatively pure form. However, none of these procedures or substances is taught in the above-described prior art.

SUMMARY OF THE INVENTION

The present invention relates to the resolution of tamsulosin enantiomers by the use of diastereomeric salts thereof, especially camphor sulfonate salts, by crystallization and to the compounds, compositions, and processes used therein and produced thereby. In particular, one aspect of the invention relates to a process comprising preferentially precipitating one diastereomeric sulfonate salt of tamsulosin from a solution containing a pair of diastereomeric sulfonate salts of tamsulosin to form diastereomeric enriched precipitate and diastereomeric enriched solute. The enriched tamsulosin free base enantiomer can be liberated from either the enriched precipitate or the enriched solute. The precipitation can be repeated with or without first liberating the free base.

Similarly, another aspect of the present invention relates to a method of separation of enantiomers of tamsulosin by fractional crystallization comprising using a chiral camphor sulfonic acid in said crystallization.

A further aspect of the invention relates to a compound selected from the group consisting of (R)-tamsulosin-(+)-camphor-10-sulfonate, (S)-tamsulosin-(+)-camphor-10-sulfonate, (R)-tamsulosin-(−)-camphor-10-sulfonate, and (S)-tamsulosin-(−)-camphor-10-sulfonate. For clarity, while these salts are diastereomers, the (R) and (S) denotation indicates the stereo configuration of the tamsulosin moiety and (+) and (−) denotation indicates the optical activity of the acid from which the diastereomeric salt was formed. These diastereomers are particularly useful in preferential precipitation according to the present invention.

Another aspect of the present invention relates to a composition comprising (R) and (S) tamsulosin or the salts thereof, wherein one of said (R) or (S) forms exceeds the amount of the other within the range of 60:40 to 95:5, preferably 65:35 to 95:5 parts by weight. Such compositions can be formed by the process of the present invention and/or are useful as substrates in the resolution process of the present invention.

A further aspect of the invention relates to racemic tamsulosin free base in a solid state. The free base is a useful starting material for the resolution process of the present invention. Typically the free base is a precipitate and is preferably in crystalline form. Crystalline tamsulsoin free base of the present invention exhibits polymorphism and two particular polymorphic forms, hereinafter identified as Form 1 and Form 2, represent preferred aspects of the present invention.

Obtaining tamsulosin free base in solid state is another aspect of the present invention. For example, the present invention includes a process for producing racemic tamsulosin free base in solid state, which comprises precipitating racemic tamsulosin free base from a solution containing racemic tamsulosin in a solvent, wherein the solvent comprises at least one of water or a lower alcohol. Preferred solvents include water, methanol, water/methanol mixtures and ethyl acetate/methanol mixtures. The tamsulosin solution can be formed by dissolving a tamsulosin residue into the solvent or by treating a tamsulosin acid addition salt with a base.

Isolation of tamsulosin free base in solid state is not limited to the racemate, however, and another aspect of the present invention relates to a process for isolation of tamsulosin free base, which comprises treating an acid addition salt of tamsulosin in a solvent with a base and precipitating tamsulosin free base from the solvent, wherein the solvent comprises water, a lower alcohol or both. The tamsulosin free base can be racemic or not. The acid addition salt is normally the hydrochloride salt but is not limited thereto and includes, for example, the camphor-10-sulfonic acid salt thereof.

An additional aspect of the present invention relates to a sulfonic acid salt of 2-(o-ethoxyphenoxy)ethylamine, especially the methane sulfonate or tosylate salts thereof, as well as to (3-aminosulfonyl-4-methoxy)phenylacetone. These compounds are novel intermediates that are useful in the production of tamsulosin free base.

BRIEF DESCRIPITION OF THE DRAWINGS

DETAILED DESCRIPTION OF THE INVENTION

Figure 1:
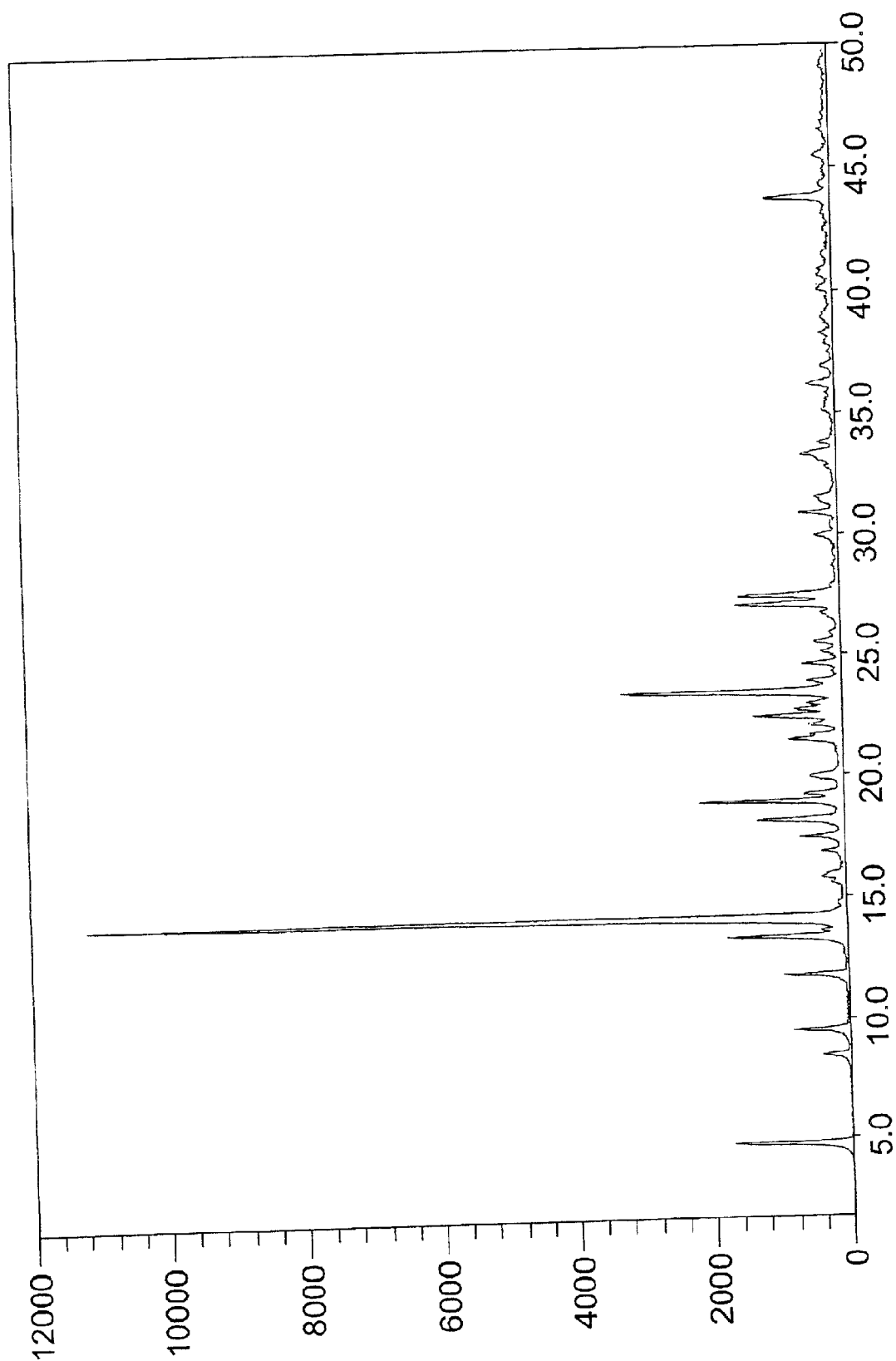
FIG. 1 is an X-ray diffraction pattern of racemic tamsulosin free base Form 1.

The present invention relates to the resolution of tamsulosin. The process of resolving tamsulosin comprises preferentially precipitating one diastereomeric sulfonate salt of tamsulosin from a solution that contains a pair of diastereomeric sulfonate salts of tamsulosin to form a precipitate that is enriched with one diastereomer and a solute (or remaining mother liquor) that is enriched with the other diastereomer. The invention is based on the discovery that diastereomeric sulfonate salts of tamsulosin are easily separated by crystallization. Such a process is sometimes referred to as fractional crystallization.

The solution that contains the diastereomers can be formed in a variety of ways. For example, tamsulosin substrate can be reacted in a solvent with a sulfonic chiral acid to form a pair of diastereomers in solution. Alternatively, a solid mixture of diastereomers such as a precipitate or a diastereomeric enriched precipitate can be dissolved in a solvent to form the solution. Thus, regardless of how the solution containing diastereomeric sulfonic acid salts of tamsulosin is formed, any preferential precipitation of one of the diastereomers from such a solution is contemplated as being within the scope of the present invention.

The substrate for the process of the invention (=tamsulosin substrate) is a mixture of tamsulosin enantiomers. The mixture of (R) and (S) enantiomers can be equimolar (50:50) as in racemic tamsulosin or a racemic mixture of tamsulosin enantiomers, or unequal. In some embodiments the amount of one enantiomer can be significantly greater than the amount of the other enantiomer, especially if the process is being applied to a tamsulosin substrate already partially resolved into enantiomers or to a substrate made by an optically specific method that has insufficient optical purity.

The applicability of the resolution process of the invention is not limited to racemic tamsulosin free base in solid state. In the substrate for resolution, tamsulosin may be present either in a form of free base or as an acid addition salt other than a salt with a chiral acid. In all these forms, tamsulosin may be applied in an isolated state, such as a crystalline or non-crystalline solid, a semisolid or liquid, or in a solution or as a product of a chemical reaction, i.e. as a raw product or reaction mixture obtained in the last step of the manufacturing process leading to it. It may be used either crude or purified by any suitable method, in any solvated or hydrated form.

The most advantageous tamsulosin substrate for the process of optical resolution is optically impure or racemic tamsulosin free base. The free base may be prepared by various processes listed below. Moreover, a novel, suitable procedure for isolating tamsulosin free base in solid state is set forth hereinafter. The solid state, particularly crystalline, form of tamsulosin free base is a preferred substrate. Additionally, it is preferred that the tamsulosin free base be in pure form, such as 80% or more pure, preferably 90% or more pure, and even 95% or more pure from non-tamsulosin impurities.

The racemic or otherwise optically impure tamsulosin substrate is converted into the diastereomeric salt pair by contacting the substrate in a suitable solvent with a suitable optically active (i.e., chiral) sulfonic acid. The chiral sulfonic acids useful within the present invention are preferably monovalent organic sulfonic acids having pKa value lower than about 3.5. Preferred chiral acids are camphor sulfonic acids including lower alkyl and/or halo derivatives thereof. Specifically preferred acids are (−)-camphor-10-sulfonic acid and (+)-camphor-10-sulfonic acid. These acids are commercially available and can be made by methods well known in the art.

The amount of the chiral acid used in forming the diastereomeric pair is typically within the range of 0.5–2 moles per 1 mole of tamsulosin and is preferably essentially equimolar.

The solvent is selected so as to facilitate the salt reaction and preferably to allow subsequent separation of the resulting diastereomers by fractional crystallization. In the process, a mixture of tamsulosin substrate (free base or salt) with a solvent may be contacted with a solid chiral acid, or a mixture of chiral acid with a solvent may be contacted with solid tamsulosin, or both partners may be combined with a solvent prior to being contacted together. The contact may be made using a single solvent or a mixture of solvents. Normally the substrate and the acid are dissolved in the solvent, even if they started as a solid at the beginning of the contact, in order to facilitate an efficient salt reaction. Suitable solvents include lower alcohols especially methanol and ethanol, acetone, dioxane, ethyl acetate, mixtures thereof, and mixtures of one or more of these solvents with water. Preferred solvents are methanol and methanol-water mixtures.

The temperature of contact is from ambient to the boiling point of the solvent system, the later being preferred. It is not required that a complete solution is formed in this step, though it is preferred.

The salt reaction forms a pair of diastereomers: one diastereomer resulting from the reaction of (R)-tamsulosin with the chiral sulfonic acid and another resulting from the reaction of the (S)-tamsulosin with the chiral sulfonic acid. One of the diastereomers is preferentially precipitated from the solvent. The precipitation is "preferential" in that the conditions used allow for one of the diastereomers to be precipitated to a greater extent than the other. The precipitation of the solid phase may be spontaneous, or may be induced by changing the conditions of the solution, e.g. by cooling the mixture after contact, adding a contra-solvent, removal of a part of the solvent or by combination of these techniques. As used herein "induced" includes partially induced such as where some precipitation occurs spontaneously and more precipitation is achieved by an inducement technique as well as precipitation achieved by only an inducement technique. The precipitation, whether spontaneous or induced, may also be facilitated by the presence of or inoculation with a seeding crystal of the desired salt.

The obtained solid salt is substantially enriched by one enantiomer of tamsulosin, advantageously by the (R)-tamsulosin. As used herein "enrichment" means that the product contains more of one of the (R)- or (S)-tamsulosin or tamsulosin diastereomer than the starting substrate or composition. For example, if the starting tamsulosin contained a 50:50 mixture of (R) and (S) enantiomers, then a precipitation of a salt having an (S):(R) tamsulosin ratio of 30:70 would be a diastereomeric enriched precipitate because the diastereomer having (or derived from) the (R)-tamsulosin has been increased relative to the amount in the initial solution. Similarly, the mother liquor is likewise enriched by the other diastereomeric salt formed from the second enantiomer, e.g. (S)-tamsulosin, and thus is a diastereomeric enriched solute. The ratio of diastereomers in the initial solution is not limited to racemic mixtures and includes solutions where one diastereomer is contained in a greater amount than the other. Preferred solutions contain diastereomers of the (R):(S)-tamsulosin in a ratio from 65:35 to 95:5 or more and typically include solutions having a ratio within the range of 70:30 to 95:5, more typically 75:25 to 85:15. In these later cases, enrichment occurs so long as the precipitate (and solute) has a different ratio of one diastereomer to the other than in the solution. For example, a solute having a ratio of diastereomeric (R):(S) tamsulosin of 87:13 is an enriched solute from a solution that contained diastereomeric (R):(S) tamsulosin of 65:35. The degree of enrichment (optical yield) is preferably at least 50%, typically at least 75%, more typically at least 80% and preferably is at least 90%.

In a preferred variant, the diastereomeric salt of the desired (R) isomer of tamsulosin with a chiral acid is less soluble than that of the diastereomer of the (S) isomer and thus the (R) form preferentially precipitates out of the solution. The precipitate may be separated from the reaction mixture by ordinary methods such as by filtration or centrifugation.

In a second variant, the salt of the desired (R)-tamsulosin isomer with a chiral acid is more soluble than that of the (S) isomer and it remains in the solution after separation of the solid. Then, the mother liquor contains the desired enantiomer of tamsulosin and may be elaborated by various ways. For instance, the solvent may be evaporated or a contrasolvent may be added to obtain the desired salt in solid state.

Advantageously, the salt is not isolated in a solid state and the obtained solution is used as such in the next step of liberation of (R)-tamsulosin from the salt. Optical yields of this variant are similar to those as above.

An example of an advantageous embodiment of the optical resolution process of the invention, substantially racemic tamsulosin reacts with (−)-camphor-10-sulfonic acid in a methanol whereby (R)-tamsulosin (−)camphor-10-sulfonate separates out from the solution as a solid, while the salt of the (S) enantiomer remains in the solution. The (R) salt may be separated from the reaction mixture after precipitation by ordinary methods e.g. by filtration or centrifugation. The diastereomeric salt may be also isolated in solvated or hydrated form.

Alternatively, the salt of the desired (R) isomer can be more soluble than the (S) isomer in which case the diastereomer containing (S)-tamsulosin is preferentially precipitated and the diastereomer containing (R)-tamsulosin preferentially remains in the solution. This case occurs, e.g., in preparing salts with (+)-camphor-10-sulfonic acid. The (R) diastereomer of tamsulosin (+)-camphor-10-sulfonate remaining in the solution may be elaborated by evaporation to obtain the salt in solid state or may be used in any subsequent process steps as it is.

Thus, because both the precipitated and the remaining dissolved diastereomers are enriched, either the precipitated or the remaining dissolved form can be used. The optical yield can be increased by re-precipitation of the diastereomeric enriched precipitate from a suitable solvent (a re-precipitation solvent); advantageously, the same kind of solvent as was used in the solution for the initial precipitation. The re-precipitation forms a further enriched precipitate and an enriched re-precipitation solute. The further enriched precipitate can be isolated by any known means as described above. Conversely, the re-precipitation solute is advantageously combined with the initial solute to enhance the yield of the non-precipitating diastereomer.

It is preferred, however, that the (R)-tamsulosin containing diastereomer be precipitated from the solvent. The precipitated enriched salt may be advantageously isolated from the reaction mixture and optionally re-precipitated or (re)crystallized before being used in any subsequent process step. If, however, the (S)-tamsulosin containing diastereomer preferentially precipitates, then the solute is accordingly enriched by the (R)-tamsulosin containing diastereomer. It is advantageous to combine such enriched solute with the liquid phase of the original reaction mixture or solution to increase the yield of the desired (R)-tamsulosin in subsequent reaction step.

Preferred diastereomeric pairs include (R)- and (S)-tamsulosin (−)-camphor-10-sulfonates and (R)- and (S)-tamsulosin (+)-camphor-10-sulfonates. Each one of these diastereomers is a specific aspect of the present invention. The (R)-tamsulosin containing diastereomer is particularly preferred. Moreover, the optical purity of such compounds is desired to be high, for example at least 75% of the salt material having the (R) tamsulosin configuration, more preferably at 80%, more preferably at least 90%, still more preferably at least 95%, and still more preferably at least 99% including 99.5% or greater.

(R)-tamsulosin(−)camphor-10-sulfonate can be isolated in a solid state as a crystalline substance. Highly pure forms solid state forms thereof preferably have at least one of the following characteristics: IR absorbance peaks of 1740, 1505, 1161 and 1044 $cm^{-1}$ (in KBr), a melting range of 208–211° C., or an optical rotation of about −17.2° (c=0.5 in methanol). Of course, the (R)-tamsulosin(−)camphor-10-sulfonate can and will have additional IR absorbance peaks as well as other physical properties not mentioned above.

The salt substantially enriched by the desired enantiomer of tamsulosin, either the precipitate or the solute, is elaborated in the next step to liberate the so enriched tamsulosin from the salt form. The liberation step essentially comprises treatment of the salt (in solid, suspended or dissolved state) with an organic or inorganic base. The base should be stronger than the basicity of tamsulosin.

The organic or inorganic base liberates both the tamsulosin and the used chiral acid from their mutual salt form and forms a new salt with such acid, while tamsulosin substantially enriched by the desired enantiomer is obtained as a free base.

The liberation step is advantageously performed in a solvent which at least partially dissolves the used salt and base. Generally, the liberation of the desired enantiomer of tamsulosin from the enriched salt proceeds by contacting the salt with an equivalent of a suitable base, e.g., metal hydroxides, in a proper solvent, advantageously in water. The so formed free base of the enriched tamsulosin is normally then isolated by ordinary methods. If water has been employed as a solvent for neutralization, the tamsulosin base precipitates as a solid and is isolated by filtration or centrifugation.

Alternatively, the salt is contacted with water, then acidified with a stronger acid, e.g. with hydrochloric acid, and the liberated resolution agent is removed by extraction with an organic solvent e.g. with ethyl acetate. Tamsulosin remains in the aqueous layer and is precipitated therefrom as a free base by alkalinization, e.g. with sodium hydroxide solution.

Any conventional method applicable to decomposition of tamsulosin salt and liberation of tamsulosin base may be employed. Advantageously, such methods are preferred that allow the isolation of, and, if advantageous, the reprocessing of the resolution agent. The resulting liberated free base preferably contains an enrichment of the (R)-tamsulosin or a salt thereof. Preferred tamsulosin compositions contain the (R):(S)-tamsulosin in a ratio from 65:35 to 99.9: to 0.1. Typical compositions containing enriched but not optically pure (R) form include an (R):(S) ratio of 65:35 to 95:5 or more and typically include solutions having a ratio within the range of 70:30 to 95:5, more typically 75:25 to 85:15.

In a preferred aspect, the obtained product comprises substantially the (R)-isomer of tamsulosin. The formed free base of tamsulosin, especially the enriched (R) enantiomer, may be further converted into an acid addition salt with a suitable acid, particularly with a pharmaceutically acceptable acid, by methods known per se. Examples of such salts are the hydrochloride, hydrobromide, acetate, fumarate, maleate, citrate or methane sulfonate.

If the optical purity of the obtained tamsulosin product is not sufficient, the resolution may be enhanced by repeating the process. The same or another chiral sulfonic acid may be employed in the repeated process. Accordingly, a second pair of diastereomeric tamsulosin can be the same or different as the first pair. In one embodiment, the second pair is different than the first such as by using a chiral sulfonic acid that is different in rotation from the first acid. In certain embodiments, it is advantageous that the first precipitation preferentially precipitates the diastereomer containing the (S)-tamsulosin and the second precipitation from a second solvent preferentially precipitates the (R)-tamsulosin containing diastereomer. In this embodiment, the enriched solute from the first precipitation is used either with or without liberation of the tamsulosin free base to make the solution for the second precipitation.

An example is as follows. Racemic tamsulosin is treated with (+) camphor-10-sulphonic acid whereby most of the undesired (S) enantiomer is separated as a solid salt with said acid and the salt with the desired (R) enantiomer remains in the liquid phase. Therefrom, the tamsulosin free base is liberated in solid state by an action of a base and is separated from the mother liquor (solute). The solid enriched by the (R) enantiomer of tamsulosin base is then treated with (−)-camphor-10-sulphonic acid to form a pair of diastereomers. The desired salt precipitates from the solution and is isolated, converted to free base and, if necessary, recrystallized. The essentially pure (R) isomer of tamsulosin is then converted into a pharmaceutically acceptable salt, e.g. to a hydrochloride salt.

Similarly, the process may be applied to tamsulosin products from a synthesis or recovered from mother liquors, which are insufficiently pure (R)-tamsulosin. In either case, the product containing the (R)-tamsulosin is accordingly treated with a suitable chiral organic sulfonic acid in a suitable solvent, fractionally crystallized to obtain an enriched diastereomer, and the optically purer product is liberated from the desired fraction of the salt. The tamsulosin free base can be converted to a pharmaceutically acceptable salt as mentioned above.

The compositions, in summary, that comprise (R)- and (S)-tamsulosin, or salts thereof, wherein one of the (R) or (S) forms is in excess to the other, can be used as starting materials or substrates for the various processes of the present invention, or can be formed as products of the processes of the present invention. Generally, the ratio of the excessive or majority form to the minority form is within the range of 60:40 to 95:5, and typically 65:35 to 95:5, parts by weight. The tamsulosin can be a salt such as a diastereomeric salt, especially camphor-10-sulfonic acid salts, or a simple pharmaceutically acceptable salt such as a hydrochloride salt. Alternatively, the tamsulosin can be a free base. The composition can be in a solid form, especially a precipitate optionally isolated and dried from the solvent or mother liquor, or in a solution form such as the solute. In one embodiment, the amount of (R)-tamsulosin is the majority and the (S)-tamsulosin is the minority. Preferred ranges for the relative amounts of (R):(S) in this embodiment are 61:39 to 87:13, more typically 65:35 to 85:15, and still more typically 75:25 to 85:15, parts by weight.

The typical starting tamsulosin substrate, namely racemic tamsulosin free base in solid state, is not formed in the prior art per se. The present invention is based in part on the discovery that the racemic free base can be formed and isolated in the solid state. Preferably the solid state form is a precipitate from a solution. More preferably, the solid state form is a crystalline form. The crystalline form includes all polymorphic modifications, unless otherwise noted and includes hydrates and solvates thereof. In particular, two polymorphic forms of solid state racemic tamsulosin free base, designated as Form 1 and Form 2, have now been discovered as part of the present invention and are described hereinafter. The solid state racemic free base can be isolated in high purity, including at least 80% purity, more preferably at least 90% purity, still more preferably at least 95% purity. Relatively pure precipitates are white or almost white microcrystalline substances, are sparingly soluble in water, are soluble in alcohols such as methanol and ethanol, and are soluble in chlorinated hydrocarbons.

Figure 3:
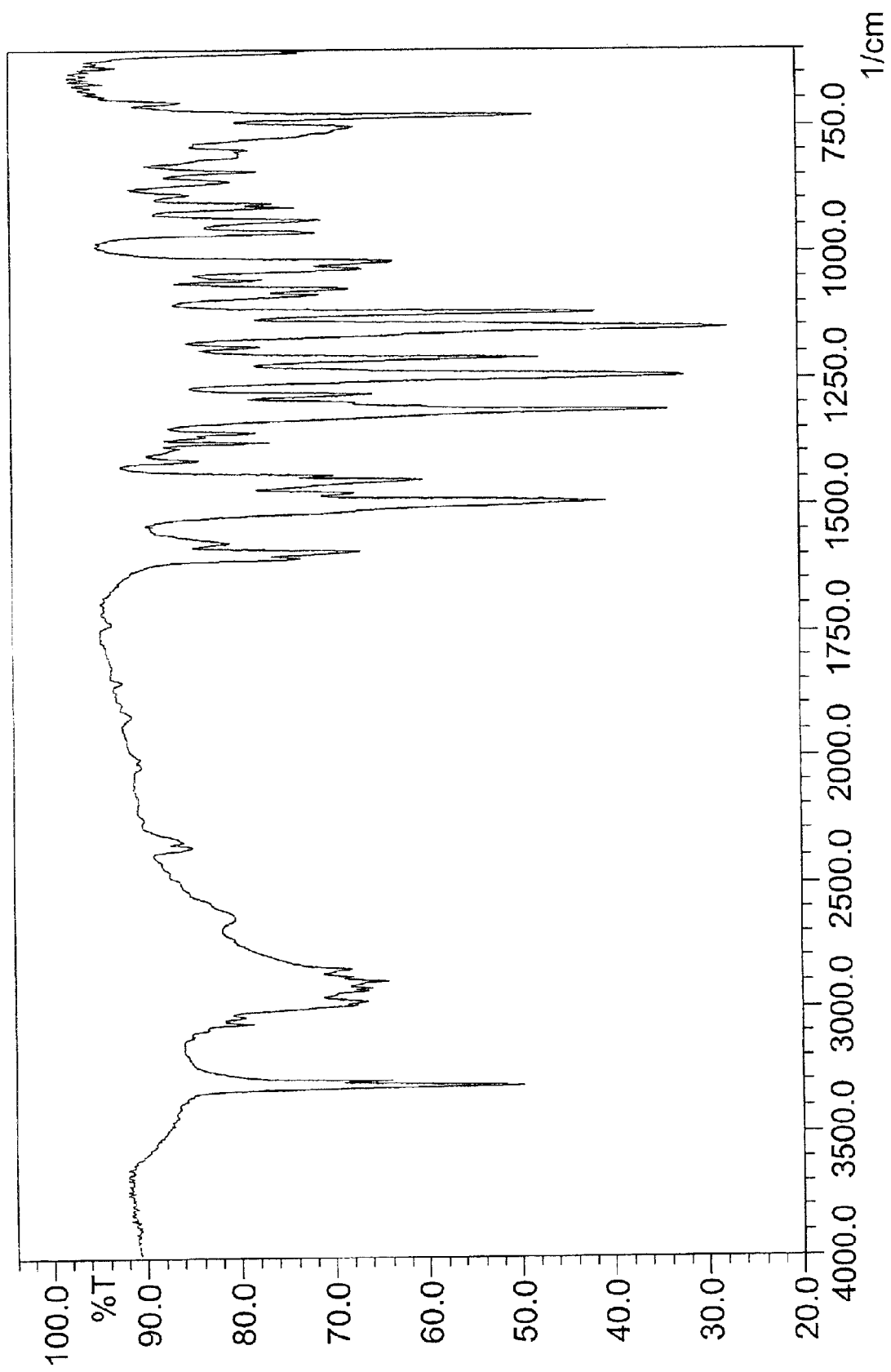
FIG. 3 is an IR spectrum of recemic tamsulosin free base Form 1 in KBr.
Figure 5:
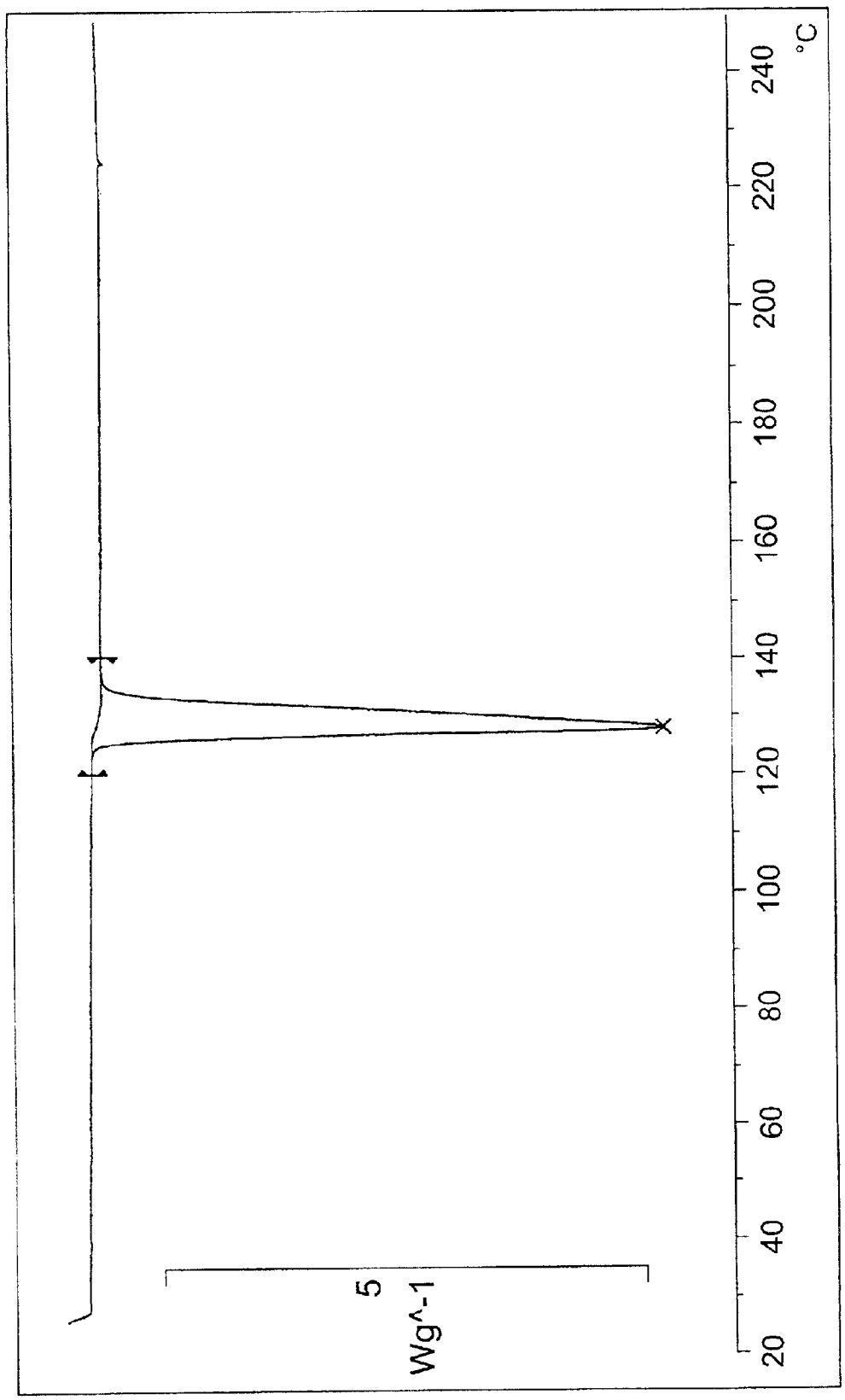
FIG. 5 is a DSC scan of racemic tamsulosin free base Form 1.

Racemic tamsulosin free base may exist in various polymorphic modifications. One such modification is designated herein as Form 1. This Form of the free base has an X-ray diffraction pattern that substantially corresponds to FIG. 1, an IR absorbance spectrum that substantially corresponds to FIG. 3, and a DSC curve that substantially corresponds to FIG. 5. Form 1 generally has a melting point of about 127–129° C. The Form 1 polymorph is obtainable, inter alia, by crystallization of tamsulosin free base from methanol/ethyl acetate mixture, but is not limited thereto.

Figure 2:
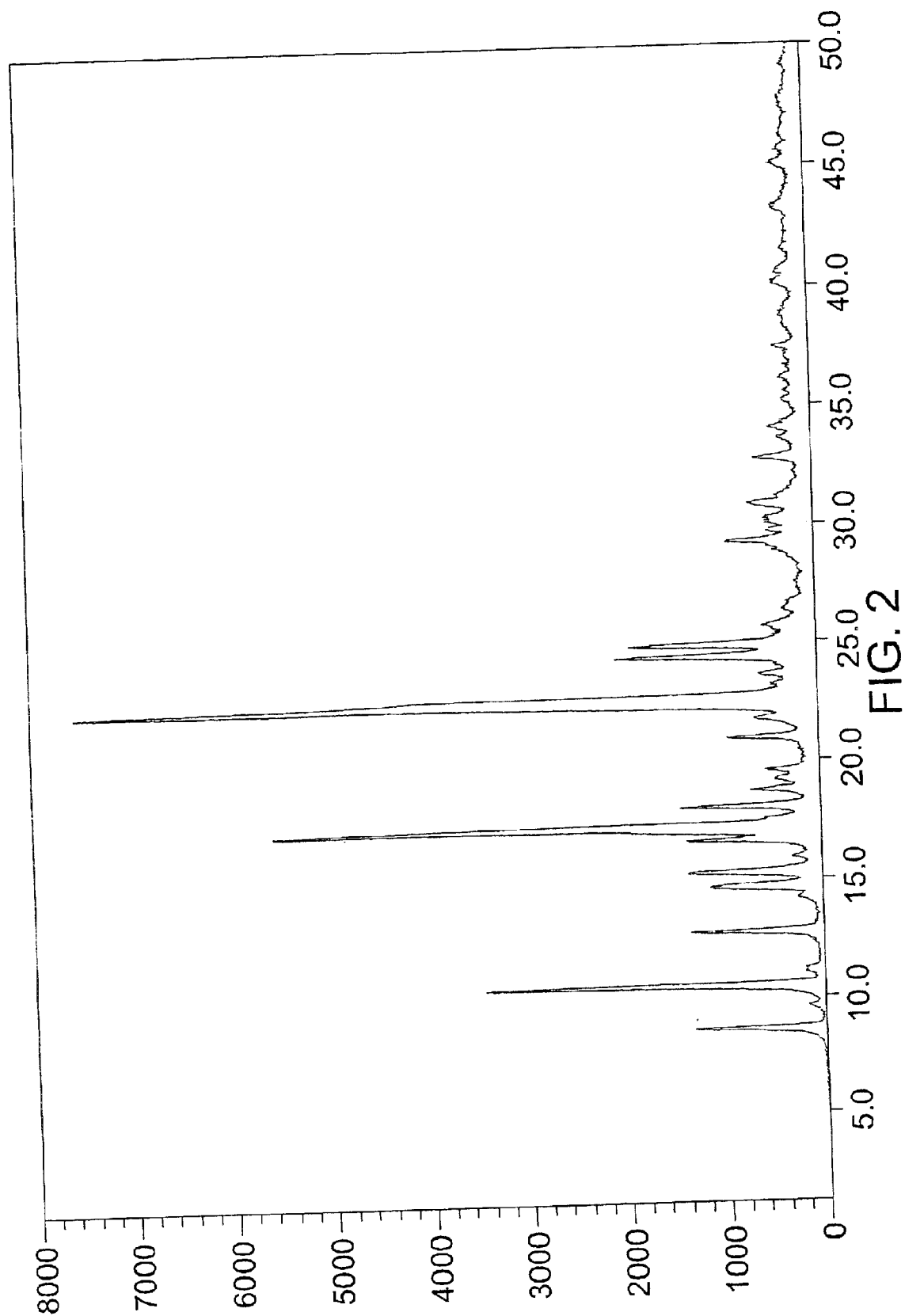
FIG. 2 is an X-ray diffraction pattern of racemic tamsulosin free base Form 2.
Figure 4:
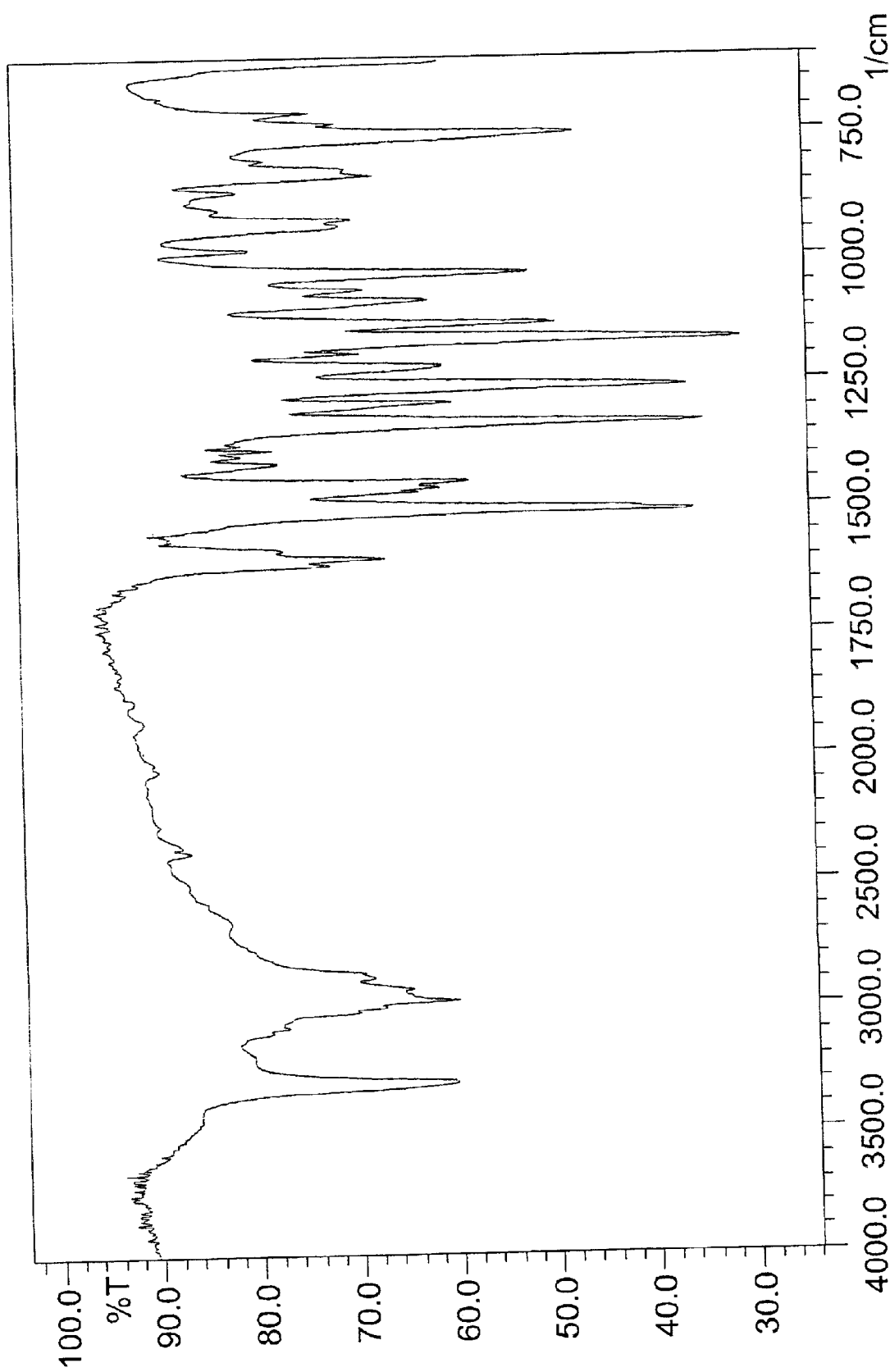
FIG. 4 is an IR spectrum of racemic tamsulosin free base Form 2 in KBr.
Figure 6:
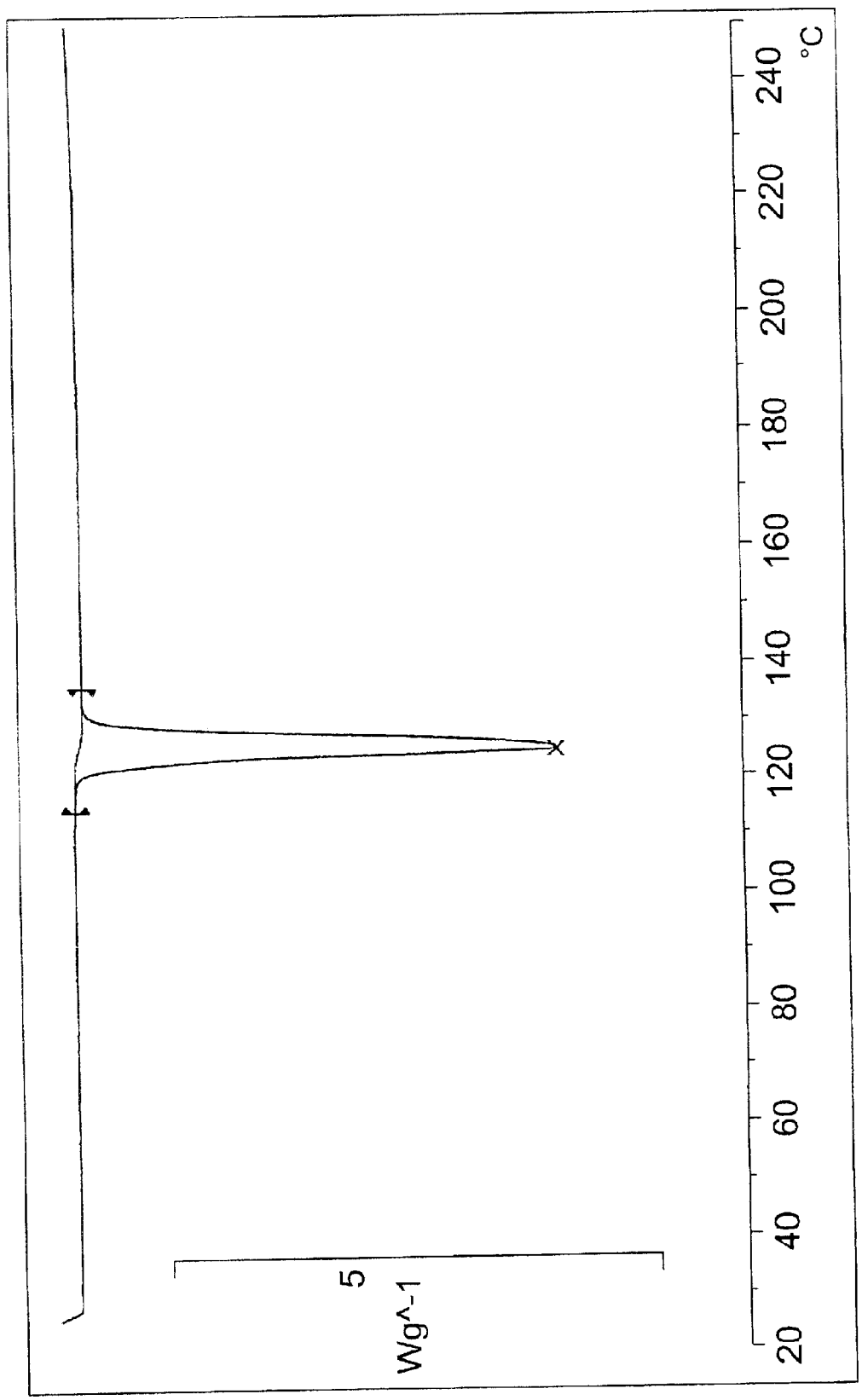
FIG. 6 is a DSC scan of racemic tamsulosin free base Form 2.

Another such modification is designated herein as Form 2. This Form of the free base has an X-ray diffraction pattern that substantially corresponds to FIG. 2, an IR absorbance spectrum that substantially corresponds to FIG. 4, and a DSC curve that substantially corresponds to FIG. 6. A comparison of the X-ray diffraction patterns in FIGS. 1 and 2 shows that the tamsulosin free base Form 1 is different from the Tamsulosin free base Form 2. This difference is confirmed by the differences in IR spectra as well. Generally Form 2 has a melting point of about 124–126° C. and FIG. 6 shows a single melting endotherm for Form 2 of about 125° C. The Form 2 polymorph is obtainable, inter alia, by precipitation of tamsulosin base after neutralization of tamsulosin hydrochloride by a sodium hydroxide, in a methanol/water mixture, but is not limited thereto.

The solid state tamsulosin free base, especially the racemic free base, can be obtained surprisingly by precipitating the free base from a solution wherein the solvent for the solution comprises at least one of water or a lower alcohol. A "lower alcohol" means an alcohol having 1 to 4 carbon atoms and is preferably methanol or ethanol. Additional solvents may also be present along with the water and/or lower alcohol, including, without limitation, an ester such as ethyl acetate, an aliphatic ketone, such as acetone or methylisobutylketone, and/or an ether, especially a water-miscible ether such as dioxan or tetrahydrofuran. Preferred solvents are water, a mixture of water and methanol, and a mixture of ethyl acetate and methanol.

Precipitation can be carried out by any conventional technique including reducing the temperature of the solution, removing a portion of the solvent, etc. In some embodiments water can be used as a contra-solvent such that upon addition of the water, optionally in conjunction with a reduction in solution temperature, precipitation occurs. In a solvent system of water and methanol, tamsulosin free base precipitates in solid state from the solution at room temperature or less.

The tamsulosin free base precipitate can be recovered by filtration and optionally dried. Further, if desired, the solid tamsulosin free base may be recrystallized from a suitable solvent.

The solution of tamsulosin can be prepared or obtained in a variety of ways. For example, a residue from the synthesis of racemic tamsulosin can be dissolved in a solvent. A "residue" refers to the tamsulosin material obtained by evaporating off all or most of the solvent, for example, the solvent used in the synthesis of the tamsulosin molecule. For example, a racemic tamsulosin free base residue can be dissolved in water, typically at temperatures above room temperature, i.e. greater than 50° C., to form the solution from which racemic tamsulosin free base can be precipitated. Similarly, a racemic tamsulosin free base residue can be dissolved in a mixture of ethyl acetate and methanol to form the solution from which racemic tamsulosin free base can be precipitated. Alternatively, the tamsulosin free base solution can be formed as a result of its synthesis; i.e., the solvent in which the tamsulosin free base is obtained is appropriate as is or upon the addition of water and/or a lower alcohol for use in the inventive precipitation process.

Alternatively the solution of racemic tamsulosin can be formed from a solution of an acid addition salt of racemic tamsulosin. The process comprises treating an acid addition salt of racemic tamsulosin with a base in a solvent that comprises at least one of water or a lower alcohol to form the solution of racemic tamsulosin. The base can be an organic or inorganic base such as an alkali metal hydroxide especially sodium hydroxide, ammonia or an organic amine. The amount of base is preferably equimolar. The preferred range of reaction temperature is from room temperature to reflux temperature. The solvent in which the treating is carried out can be formed in situ, e.g., water can be supplied concurrently with the base to a solution of racemic tamsulosin free base in an organic solvent.

A particular embodiment of this process comprises treating an acid addition salt of tamsulosin in a solvent with base and precipitating tamsulosin free base from the solvent, wherein the solvent comprises water, a lower alcohol or both. This process is useful for both racemic tamsulosin such as racemic tamsulosin HCl as well as non-racemic and/or enantiomerically enriched camphor-10-sulfonate salts of tamsulosin. In either event, a solid free base form is obtained. The base and the treating conditions are the same as described above.

The tamsulosin salt-containing solution can be formed via the synthesis of tamsulosin or can be formed by dissolving an available solid form of the salt, e.g. a commercially available tamsulosin salt, in a solvent.

The precipitated tamsulosin free base is generally formed in high purity, typically at least 80%, more typically at least 90% and preferably at least 95% pure. This purity is based on the isolated and dried solid precipitate as is conventional in the art. If desired, the solid form tamsulosin free base can be recrystallized to improve its purity. In an example, the tamsulosin free base may be recrystallized from a solvent comprising a lower alcohol such as methanol, for instance from a mixture of methanol and ethyl acetate, or from a mixture of methanol and water.

Racemic tamsulosin or a salt thereof can be prepared by any suitable synthesis technique. Three preferred processes are described below in detail.

In a first process ("Process A"), racemic tamsulosin free base may be prepared by reductive amination of the ketone of formula (4) by the amine of formula (5).

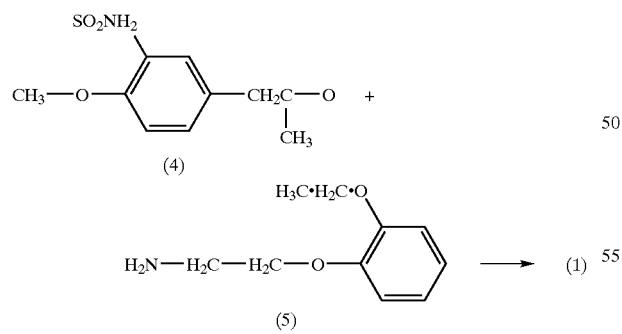

The (3-aminosulfonyl-4-methoxy)phenylacetone (4) is a novel compound and it may be prepared in analogy to a process described in U.S. Pat. No. 544,958 for related compounds. The starting compound is 4-methoxyphenyl acetone which is chlorosulfonated by chlorosulfonic acid at 0–5° C. After treating the reaction mixture with water, the resulting 3-chlorosulfonyl-4-methoxyphenylacetone (9) is formed in solid state and is isolated by filtration. The compound (9) is then treated in ethyl acetate solution with aqueous ammonia at 5° C. The formed crystals of crude (4) are recovered by filtration. The crude (4) may be purified by crystallization, e.g. from ethanol.

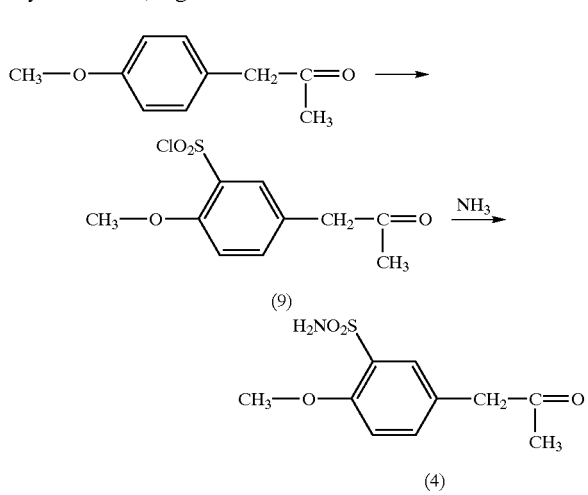

The 2-(o-ethoxyphenoxy)ethylamine (5) may be prepared according to a process described in BE 668124. In said process, 2-ethoxyphenol (10) reacts for 16-24 hours with chloroacetonitrile in refluxing acetone under presence of potassium carbonate. After filtration and evaporation of the solvent, the oily residue is dissolved in a suitable solvent such as ethanol or ether, treated with water and with a base such as ammonia or sodium hydroxide solution and crude o-ethoxyphenoxyacetonitrile (11) is obtained by evaporation of the solvent or by crystallization from the solvent. The crude (11) may be recrystallized from a suitable solvent, e.g. ethanol/water mixture. The compound (11) is catalytically hydrogenated under elevated pressure in a suitable solvent, e.g. toluene or toluene/triethylamine solution, using Raney cobalt or any other suitable catalyst. Crude free base of 2-(o-ethoxyphenoxy)ethylamine (5) is obtained after filtration and evaporation of the solvent as an oil.

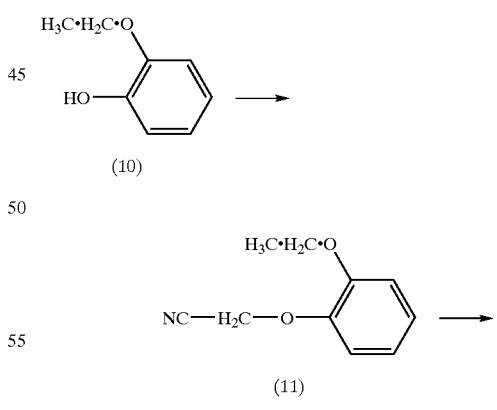

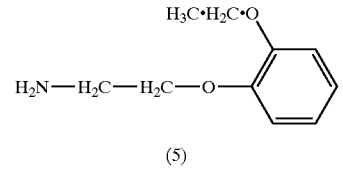

It has now been discovered that the so obtained free base of (5) is contaminated by side-products and should be purified for the next step. However, normal alkaline extraction surprisingly resulted in too high a loss. The amine (5) has unexpectedly high water solubility for an amine compound. It has been discovered that an effective way to purify the amine is to form a sulfonic acid salt of the amine, especially methane sulfonate or tosylate. The salt, particularly the methane sulfonate salt of (5), may be isolated in solid, preferably crystalline state by conventional methods and may be used as an advantageous substrate in the next reaction step. The conversion of the free base of (5) into an acid addition salt and isolation of the salt in solid state enhances the purity of the compound (5), particularly it removes side products that resulted from hydrogenation such as 2-ethoxyphenol. The 2-(o-ethoxyphenoxy) ethylamine methane sulfonate thus forms a specific aspect of this invention.

The racemic tamsulosin is obtained by reductive aminolysis of the ketone (4) with the free base of amine (5), for instance according to the process of U.S. Pat. No. 4,558,156. If a salt of the amine (5) is used for the reaction, this salt is first converted to a free base by treatment with a suitable base, e.g. by sodium methoxide in methanol. An imino-compound is first prepared by contacting of both components in methanol. Hydrogenation catalyst such as platinum oxide or palladium/carbon is added to the reaction mixture and the mixture is hydrogenated by gaseous hydrogen, advantageously under enhanced pressure. After filtering off the catalyst, the reaction mixture is preferably acidified with an acid, preferably with alcoholic or aqueous HCl, thereby forming an acid addition salt of racemic tamsulosin, preferably tamsulosin hydrochloride. The racemic tamsulosin salt is isolated in solid form, preferably crystalline form by evaporation of the solvent or by crystallization from the solvent. The racemic tamsulosin salt is then treated with base and tamsulosin free base is precipitated as described above.

In a second process ("Process B"), racemic tamsulosin hydrochloride may be prepared in a form of a hydrochloride salt from hydroxy-tamsulosin of formula (8) according to a method of EP 34432. Starting hydroxy-tamsulosin (8) may be prepared from the amine compound (5) according to U.S. Pat. No. 4,217,305. The process comprises, in a first step, conversion of the hydrochloride salt of hydroxy-tamsulosin (8) into a chloro-tamsulosin hydrochloride (12) by means of reaction of (8) with thionylchloride in acetonitrile, and isolation of the product from the reaction mixture after its spontaneous crystallization from the reaction mixture. The compound (12) is subsequently dehalogenated by, e.g., catalytic hydrogenation using palladium on carbon as the catalyst at normal temperature and pressure. After concentration of the reaction mixture, crystalline tamsulosin hydrochloride is obtained and it may be recrystallized from a mixture of methanol and ethanol.

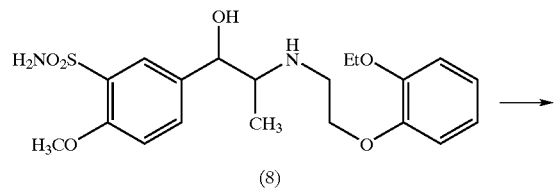

To obtain racemic tamsulosin free base in solid state, the procedure of the present invention disclosed above should be applied.

In a third process ("Process C"), racemic or partly enriched tamsulosin free base may be prepared by condensation of the racemic amine of the formula (6) with a bromo-compound of the formula (7a) in refluxing methanol.

The conditions of the manufacturing procedure were disclosed in U.S. Pat. No. 5,447,958, however, the starting amine (6) used therein was optically active. Tamsulosin free base (optically active) was obtained after separation of the reaction mixture by column chromatography in solid state and converted to hydrochloride. The column chromatography however makes this process impractical for industrial scale production of racemic tamsulosin free base.

However, it has been discovered that the process should be modified in such a way that a dipolar aprotic solvent such as dimethylformamide is used for the condensation of racemic amine (6) with (7a) and the reaction temperature is between 70 and 100° C. After removal of the solvent by distillation under reduced pressure, hot water is added to the solid residue and tamsulosin free base is allowed to crystallize by decreasing the temperature. The obtained solid product may be further purified by extraction of the side products by hot water. Optionally, tamsulosin free base may be converted to tamsulosin hydrochloride by methods known per se and recovered back from the hydrochloride by a process given above. Starting reactants may be prepared by methods known in the art.

Alternatively, the tamsulosin free base may be prepared from the racemic amine (6) by reductive amination of the aldehyde (7b); the manufacturing conditions including the synthesis of the starting aldehyde are described in AT 397960.

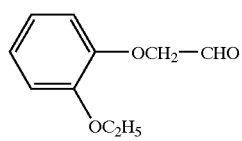

(7b)

It should be noted that this Process C may also provide for a mixture of enantiomers of tamsulosin, if the starting amine (6) was provided as a mixture of enantiomers (e.g. by incomplete optical resolution) or if the reaction conditions caused some degree of racemization. Such tamsulosin product, as discussed above, is also a suitable substrate for the resolution process of the invention.

Optically pure or substantially pure (R)-tamsulosin, acid addition salts thereof and particularly (R)-tamsulosin hydrochloride prepared by the process of the invention are useful in the preparation of medicaments for treatment of various diseases or conditions including cardiac insufficiencies and benign prostatic hyperplasia among others. It may be used alone or in combination with other active components. Such medicaments may be formulated for peroral, transdermal or parenteral application, for instance in a form of tablets or capsules. The formulations comprise therapeutically effective amounts of the active substance together with a pharmaceutically acceptable carriers or diluents and may be prepared by any conventional method.

The present invention is more particularly described and explained by the following examples. It is to be understood, however, that the present invention is not limited to these examples and various changes and modifications may be made without departing from the scope of the present invention.

EXAMPLE 1

Synthesis of Racemic Tamsulosin Free Base a) Synthesis of 2-Methoxy-5-(2-oxopropyl) benzenesulfonamide (4)

Chlorosulfonic acid (426 g, 3.656 mol) is cooled down to −10–(−15)° C. 4-methoxyphenylacetone (100 g, 0.609 mol) is added in such a rate as not to exceed temperature 5° C. in reaction mixture. After addition of all amount of methoxyphenylacetone the reaction mixture is allowed to warm up to room temperature. Mixture is stirred for 2 hours at room temperature. The reaction mixture is then poured on stirred mixture of ice (1500 g) and water (1600 ml). Formed crystals are filtered, washed with cold water (200 ml).

The crystals are dissolved in ethyl acetate (300 ml). Aqueous ammonia (600 ml) is cooled down to −5° C. and the above ethyl acetate solution is gradually added in such a rate as not to exceed 5° C. The mixture is then allowed to warm to room temperature and stirred overnight. Formed crystals are filtered, washed with water (200 ml) and ethanol (100 ml). Crystals of the crude product were recrystallized from ethanol to give 65 g of title compound.

b) Synthesis of (2-Ethoxyphenoxy)methyl cyanide (11)

Potassium carbonate (550 g, 3.98 mol) was added to acetone (1800 ml) and resulting suspension was stirred for 30 min. 2-Ethoxyphenol (460 g, 3.329 mol) was gradually added under stirring. The mixture was heated to reflux. Chloroacetonitrile (275 g, 3.642 mol) was added and the mixture was stirred under reflux for 24 hours. The reaction mixture was cooled down to room temperature. Solid was filtered off, washed with acetone (750 ml) and combined filtrates were evaporated to give oil. The oil was dissolved in ethanol (180 ml), the solution was heated to reflux and mixture of water (530 ml) and aqueous ammonia (45 ml) was added. The mixture was cooled to 5–10° C. under stirring. Crude crystalline product was filtered, washed with mixture of ethanol (250 ml) and water (400 ml). The crude product was recrystallized from ethanol /water mixture to give pure product (500 g).

c) Synthesis of 2-(2-Ethoxyphenoxy)-1-ethanamine (5) methanesulfonate (2-Ethoxyphenoxy)methyl cyanide (400 g, 2.257 mol) was dissolved in toluene (750 ml) and the solution was transferred to autoclave. 125 g of Raney cobalt was added to autoclave and the mixture was hydrogenated at 30–40° C. and hydrogen pressure 1.7 to 1.2 Mpa for one hour. The catalyst was removed by filtration and the filtrate was evaporated to give an oil.

The oil was dissolved in ethyl acetate (550 ml) and methanesulfonic acid (150 g) was added under stirring. The temperature was maintained between 20–25° C. Formed crystals were filtered, washed with ethyl acetate (250 ml) and dried 40° C. to give 430 g of the title product.

d) Synthesis of Racemic Tamsulosin Hydrochloride:

2-(2-Ethoxyphenoxy)-1-ethanamine methanesulfonate (300 g, 1.08 mol) is dissolved in methanol (1000 ml) at 40–50° C. Solution of sodium methoxide (30% soln, 195 g) is added under stirring. The mixture is cooled to 20–15° C. Formed sodium methanesulfonate is filtered off, and washed on filter with methanol (2×100 ml). Combined filtrates are transferred to autoclave. 2-Methoxy-5-(2-oxopropyl) benzenesulfonamide (263.3 g, 1.08 mol) is added and the suspension is stirred for 20 min. Catalyst Pt/C (5% Pt, 60 g) is added and the mixture is hydrogenated at 50–56° C. and at hydrogen pressure 1.7 to 1.2 Mpa for 1.5 hour. The catalyst was removed by filtration and hydrochloric acid (37%, 90 g) was added to the filtrate under stirring. Formed crystals of tamsulosin hydrochloride were filtered, washed with methanol (500 ml) and dried at 50° C. to give 360 g of title compound.

e) Synthesis of Racemic Tamsulosin Free Base

The crystals obtained in step d) were suspended in methanol (1100 ml), the mixture was heated to reflux and sodium hydroxide solution (2M, 440 ml) was gradually added followed by water (350 ml). The mixture was cooled down to 10–15° C. Formed crystals were filtered and washed on filter with methanol (150 ml) and water (150 ml) mixture. Crystals were dried at 50° C. to give 340 g of product.

EXAMPLE 2A

Synthesis of Racemic Tamsulosin Free Base 5-(-2-aminopropyl]-2-methoxybenzenesulfonamide (200 g) was dissolved in dimethylformamide (950 ml) and 1-(2-Bromoethoxy)-2-ethoxybenzene (100.3 g) was added. The reaction mixture was heated to 80–85° C. for 4 hours. Dimethylformamide was then distilled off under vacuum. Water (1000 ml) was added to solid residue and the mixture was heated to 80–90° C. under stirring for 2 hours. The mixture was cooled to room temperature. Formed crystals were filtered off and were suspended in water (900 ml). Suspension was heated to 80–90° C. under stirring for 2 hours. Crystals were filtered, washed with water (200 ml) and dried to give tamsulosin base (150 g, 89.8%).

EXAMPLE 2B

Purification of Racemic Tamsulosin Free Base 53.3. g of tamsulosin free base was dissolved, under reflux in 370 ml of a ethyl acetate/methanol mixture (56:44 w/w). The obtained solution was allowed to cool, under formation of a precipitate. The mixture was cooled to 15–20° C. and stirred 30 minutes at this temperature. The solid was isolated by filtration, washed with the solvent mixture and dried. Yield: 45.3. g. Solid state properties of the product correspond to Form 1.

EXAMPLE 2C
Purification of Racemic Tamsulosin Free Base

Tamsulosin free base (159 g) (purity 94%) was suspended in a methanol (280 ml)/water mixture (280 ml). The mixture was heated to reflux until all material dissolved. Hydrochloric acid (37%, 44 g) was added and the mixture was gradually cooled down to 0° C. Formed crystals were filtered off, washed with cold methanol (70 ml). Wet crystals were suspended in methanol (450 ml) and the mixture was heated to reflux. Aqueous sodium hydroxide (2M, 150 ml) was then added. The mixture was cooled down and water (140 ml) was added. Formed crystals were filtered off, washed with methanol-water mixture (1:1, 100 ml) and dried. Yield 117 g of a crystalline product (70%, purity 99.7%). Solid state properties of the product correspond to Form 2.

Identification of Tamsulosine Free Base

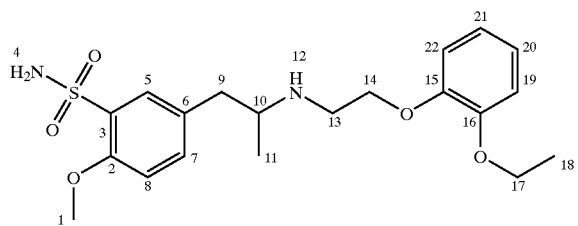

$^1$H-NMR Spectrum:

The $^1$H-NMR spectrum was measured at 303.2 K on a Bruker Avance-400 in deuterated dimethylsulfoxide at 400 MHz.

| δ | assignment |
|---|---|
| 0.95 | (d, 3H, $J_{10,11}$ = 6.3 Hz, H-11); |
| 1.30 | (t, 3H, $J_{17,18}$ = 7.0 Hz, H-18); |
| 2.48 | (dd, 1H, $J_{9,10}$ = 7.3 Hz, $J_{9,9}$ = 13.4 Hz, 1 × H-9); |
| 2.77 | (dd, 1H, $J_{9,10}$ = 5.3 Hz, $J_{9,9}$ = 13.4 Hz, 1 × H-9); |
| 2.90 | (m, ~3H, H-10 + H-13); |
| 3.89 | (s, 3H, H-1); |
| 4.01 | (m, 4H, H-14 + H-17); |
| 6.89 | (m, 2H, H-20 + H-21); |
| 6.96 | (m, ~2H, H-19 + H-22); |
| 7.01 | (bs, 1–2H, H-4); |
| 7.11 | (d, 1H, $J_{7,8}$ = 8.6 Hz, H-8); |
| 7.40 | (dd, 1H, $J_{5,7}$ = 2.3 Hz, $J_{7,8}$ = 8.6 Hz, H-7); |
| 7.58 | (d, 1H, $J_{5,6}$ = 2.3 Hz, H-5). |

$^{13}$C-NMR Spectrum:

The $^{13}$C-NMR spectrum was measured at 303.2 K on a Bruker Avance-400 in deuterated dimethylsulfoxide at 100.6 MHz.

| δ | assignment |
|---|---|
| 14.66 | (C-18); |
| 19.66 | (C-11); |
| 41.25 | (C-9); |
| 45.56 | (C-13); |
| 53.87 | (C-10); |
| 55.92 | (C-1); |
| 63.87 | (C-17); |
| 69.01 | (C-14); |
| 112.32 | (C-8); |
| 114.09, 114.68 | (C-19, C-22); |
| 120.88, 121.19 | (C-20, C-21); |
| 127.96 | (C-5); |
| 130.82, 131.09 | (C-3, C-6); |
| 134.11 | (C-7); |
| 148.38, 148.56 | (C-15, C-16); |
| 154.18 | (C-2). |

EXAMPLE 3
Resolution of Tamsulosin Free Base with (−) Camphor-10-sulfonic Acid 100 mg of racemic tamsulosin free base and 58 mg of (−)camphor-10-sulphonic acid were dissolved in 12 ml of ethanol while heating. The solution was allowed to cool to room temperature and stored overnight. The formed solid was filtered off, washed with 1 ml of ethanol and 2 ml of ether and dried.

Optical purity (HPLC): 61.3% of R-tamsulosin (−) camphor-10-sulfonate. After recrystallization from ethanol, the optical purity increased to 68.7%.

EXAMPLE 4
Resolution of Tamsulosin Free Base with (+)Camphor-10-sulphonic Acid 2.0 g of racemic tamsulosin free base and 1.71 g of (+)camphor-10-sulphonic acid was dissolved in 45 ml of methanol at reflux. The solution was slowly cooled up to 4C. The formed crystals were collected by filtration. Optical purity (HPLC): 75% of (S)-tamsulosin-(+)camphor-10-sulphonate.

640 mg of the product were recrystallised from 5 ml of methanol. After standing overnight, the formed crystals were collected by filtration and dried. Optical purity (HPLC): 94% of (S)-tamsulosin-(+)camphor-10-sulphonate.

300 mg of the product were recrystallised form 3 ml of methanol. After standing overnight at 30C., the formed crystals were collected by filtration, washed with ethanol and dried. Optical purity (HPLC): 96.5% of (S)-tamsulosin-(+)camphor-10-sulphonate.

EXAMPLE 5
Resolution of Racemic Tamsulosin Base by a Process Employing Combination of (+)- and (−) Camphor-10-sulfonic Acids.

a)

1200 g of racemic tamsulosin free base was suspended in 4700 ml of methanol and the mixture was heated to reflux. A solution of 682.4 g of (+)-camphor-10-sulfonic acid in 4700 ml of water was added to the mixture. Resulted mixture was heated to reflux and allowed to cool under stirring. At about 45° C., a solid started to precipitate. The mixture was cooled to 20–25° C. a stirred at this temperature for 5 hours. Crystalline solid was filtered out, washed with 200 ml of cold (0° C.) methanol and dried.

The solid product was suspended in 3050 ml of 50% aqueous methanol, heated to reflux and allowed to cool under stirring. After a solid began to precipitate (at approx. 55° C.), the mixture was cooled to 20–25° C. and stirred for 5 hours. The crystalline product was filtered out, washed with 150 ml of cold (0° C.) methanol and dried. Yield: 693.4 g of (S)-tamsulosin (+) camphor-10-sulfonate.

b)

Mother liquors from both crystallizations were collected and 1020 ml of 2N aqueous solution of NaOH was added under stirring until the mixture was the slightly alkaline (pH 9–10). The resulting suspension of tamsulosin base was cooled to 0–5° C. for 2 hours, filtered, washed with water and dried.

Yield: 697.5 g of tamsulosin free base comprising 76% of the (R)-enantiomer.

c)

The obtained tamsulosin free base was suspended in 1920 ml of methanol and heated to reflux. A solution of 396.6 g of (–)camphor-10sulfonic acid in 1920 ml of water was added to the boiling suspension. Reaction mixture was heated to reflux and allowed to cool under stirring. After a solid started to precipitate (approx. 35° C.), the suspension was cooled to 20–25° C. and stirred for 5 hours. Crystalline precipitate was filtered out, washed with cold methanol and dried. Yield:806.8 g of tamsulosin (–)camphor-10-sulfonate comprising 89.7% of the (R) enantiomer.

d) Recrystallization of Raw (R)-tamsulosin (–)Camphor-10-sulphonate

General Procedure:

Raw (R)-tamsulosin (–)camphor-10-sulphonate was dissolved under stirring in 3.5parts (by volume) of 50% aqueous methanol at reflux. The solution was allowed to cool until a solid began to separate and then cooled to 20–25° C. The mixture was stirred for 5 hours and the solid was separated by filtration. The solid was washed by 1.5 parts (by volume) of cold (0° C.) methanol and dried. The crystallization process was repeated several times with the following results

| Crystallization No. | Yield of crystallization | Content of R-isomer |
|---|---|---|
| 0 |  | 89.7% |
| 1 | 63.6% | 95.7% |
| 2 | 56.9% | 98.4% |
| 3 | 51.7% | 99.5% |
| 4 | 47.4% | 99.8% |

The product of the last crystallization had a melting range of 208–211 C. and optical rotation of –17.2° (c=0.5 in methanol). IR spectrum in KBr exhibits peaks of, i.a., 1740, 1505,1161 or 1044 $cm^{-1}$. Its identity was proven by NMR spectrum.

EXAMPLE 6

Conversion of (R)-tamsulosin(–)Camphor-10-sulfonate to (R)-tamsulosin Free Base 518.3 g of (R)-tamsulosin (–) camphor-10-sulfonate (opt. purity 99.8%) was dissolved under reflux in 3100 ml of 50% aqueous methanol and 445 ml of 2N aqueous NaOH was added while hot. The resulted suspension was cooled to 0–5° C. for 2 hours. The solid was filtered out, washed by water and dried. Yield : 315 g of (R)-(–)-tamsulosin free base containing 99.9% of R-isomer.

The product was dissolved under reflux in 3500 ml of 50% aqueous methanol and allowed to cool to 20–25° C. under stirring. The suspension was stirred for 8 hours. The solid was filtered off, washed with 500 ml of water and dried. Yield: 309.11 g (R)-(–)-tamsulosin free base comprising more than 99.9% of R-isomer.

EXAMPLE 7

Conversion of (R)-tamsulosin Free Base Into (R)-tamsulosin Hydrochloride 309.11 g of (R)-(–)-tamsulosin free base was suspended in 1080 ml of 50% aqueous methanol, heated to reflux and treated with 125 ml of concentrated hydrochloric acid under stirring. The resulted solution was cooled, whereby a solid crystallized. Resulted suspension was cooled to 0–5° C. for 1.5 hours. Solid product was filtered off, washed with 500 ml of cold (0° C.) methanol and dried. Yield: 320 g of (R)-(–)-tamsulosin hydrochloride comprising more than 99.9% of R-isomer.

The invention having been thus described, it will be obvious to the worker skilled in the art that the same may be varied in many ways without departing from the spirit of the invention and all such modifications are included within the scope of the present invention as set forth in the following claims.

We claim:

1. A process, which comprises:
   (a) preferentially precipitating one diastereomeric camphor sulfonate salt of tamsulosin from a solution containing a pair of diastereomeric camphor sulfonate salts of tamsulosin to form diastereomeric enriched precipitate and diastereomeric enriched solute.

2. The process according to claim 1, wherein said pair of diastereomeric sulfonate salts of tamsulosin are tamsulosin camphor-10-sulfonates.

3. The process according to claim 2, wherein said pair of salts are (R and S)-tamsulosin-(+)-camphor-10-sulfonate or (R and S)-tamsulosin-(–)-camphor-10-sulfonate.

4. The process according to claim 1, wherein said precipitation occurs spontaneously after formation of said solution of diastereomeric pairs.

5. The process according to claim 1, wherein said precipitation is induced.

6. The process according to claim 1, wherein said solution contains more of one diastereomeric salt than the other.

7. The process according to claim 1, which further comprises forming said solution by dissolving a solid mixture of a pair of diastereomeric sulfonate salts of tamsulosin in a solvent.

8. The process according to claim 7, wherein said mixture contains more of one diastereomeric salt than the other.

9. The process according to claim 1, which further comprises dissolving a solid mixture of (R) and (S) tamsulosin free base in a solvent and reacting said free base with a camphor sulfonic acid to form said solution containing a pair of diastereomeric camphor sulfonate salts of tamsulosin.

10. The process according to claim 9, wherein said tamsulosin free base contains more (R)-tamsulosin than (S)-tamsulosin.

11. The process according to claim 10, wherein said mixture contains (R)- and (S)-tamsulosin within the weight ratio of 75:25 to 95:5, respectively.

12. The process according to claim 1, wherein said solution contains a solvent selected from the group consisting of alcohols, mixtures thereof, and mixtures of one or more alcohols with water.

13. The process according to claim 12, wherein said solvent is ethanol, methanol, or a methanol and water mixture.

14. The process according to claim 1, which further comprises:
   (b) liberating tamsulosin free base from one of said diastereomeric enriched precipitate or solute to form optically enriched tamsulosin free base.

15. The process according to claim 14, which further comprises:
   (c) reacting said optically enriched tamsulosin free base with a camphor sulfonic acid to form a pair of diastereomeric camphor sulfonate salts of tamsulosin in a second solution and (d) preferentially precipitating one of said pairs from said second solution to form a diastereomeric enriched second precipitate and a diastereomeric enriched second solute.

16. The process according to claim 15, wherein said diastereomeric pair of tamsulosin in step (a) is the same salt as the pair in step (d).

17. The process according to claim 15, wherein said diastereomeric pair of tamsulosin in step (a) is a different salt than said pair in step (d).

18. The process according to claim 17, wherein the difference in the salts is the optical rotation of the corresponding camphor sulfonic acids.

19. The process according to claim 18, wherein one diastereomeric pair is (R and S)-tamsulosin-(+)-camphor-10-sulfonate and the other is (R and S)-tamsulosin-(−)-camphor-10-sulfonate.

20. The process according to claim 19, wherein the diastereomeric pair in step (a) is the (R and S)-tamsulosin-(+)-camphor-10-sulfonate and the diastereomeric pair in step (d) is the (R and S)-tamsulosin-(−)-camphor-10-sulfonate.

21. The process according to claim 20, wherein (S)-tamsulosin-(+)-camphor-10-sulfonate is precipitated in step (a) and (R)-tamsulosin-(−)-camphor-10-sulfonate is precipitated in step (d).

22. The process according to claim 15, wherein the said liberation step (b) is performed on said diastereomeric enriched solute.

23. The process according to claim 22, wherein the diastereomer containing the (S)-tamsulosin is preferentially precipitated in step (a) and the diastereomer containing the (R)-diastereomer is preferentially precipitated in step (d).

24. The process according to claim 15, which further comprises:
(e) liberating tamsulosin free base from one of said diastereomeric enriched second precipitate or second solute to form optically enriched tamsulosin free base.

25. The process according to claim 14, which further comprises re-precipitating said enriched precipitate from a re-precipitation solvent to form a further enriched precipitate and an enriched re-precipitation solute.

26. The process according to claim 25, wherein said liberation step (b) liberates the tamsulosin contained in said enriched solvent and said enriched re-precipitation solvent.

27. The process according to claim 14, wherein said optically enriched tamsulosin free base is converted to a pharmaceutically acceptable salt thereof.

28. The process according to claim 27, wherein said salt is enriched (R)-tamsulosin hydrochloride.

29. A method of separation of enantiomers of tamsulosin by fractional crystallization comprising using a chiral camphor sulfonic acid in said crystallization.

30. A compound selected from the group consisting of (R)-tamsulosin-(+)-camphor-10-sulfonate, (S)-tamsulosin-(+)-camphor-10-sulfonate, (R)-tamsulosin-(−)-camphor-10-sulfonate, and (S)-tamsulosin-(−)-camphor-10-sulfonate.

31. The compound according to claim 30, which is (R)-tamsulosin(−)camphor-10-sulfonate.

32. A compound according to claim 31, having at least one of the following characteristics: IR absorption peaks in KBr of 1740, 1505, 1161 and 1044 $cm^{-1}$, melting range of 208–211° C. or an optical rotation of about −17.2° (c=0.5 in methanol).

33. The process according to claim 1, wherein said camphor sulfonate salts of tamsulosin are formed from camphor sulfonic acid, a lower alkyl derivative of camphor sulfonic acid, or a halo derivative of camphor sulfonic acid.

34. The process according to claim 3, wherein said solution contains a solvent selected from the group consisting of alcohols, mixtures thereof, and mixtures of one or more alcohols with water.

35. The process according to claim 34, wherein said solvent is ethanol, methanol, or a methanol and water mixture.

36. The process according to claim 15, wherein said second solution contains a solvent selected from the group consisting of alcohols, mixtures thereof, and mixtures of one or more alcohols with water.

37. The process according to claim 20, wherein said solution of said step (a) and said second solution of said step (c) each independently contain a solvent selected from the group consisting of alcohols, mixtures thereof, and mixtures of one or more alcohols with water.

38. The process according to claim 37, wherein said solvent is selected from the group consisting of methanol and methanol and water mixtures.

* * * * *